(12) United States Patent
Szolajska et al.

(10) Patent No.: US 8,765,666 B2
(45) Date of Patent: Jul. 1, 2014

(54) ADENOVIRUS DODECAHEDRON PARTICLES FOR DELIVERY OF PHARMACEUTICAL AGENTS

(75) Inventors: Ewa Szolajska, Warsaw (PL); Jadwiga Chroboczek, Warsaw (PL); Monika Zochowska, Warsaw (PL)

(73) Assignee: Instytut Bio chemii i Biofizki PAN, Warszawa (PL)

( * ) Notice: Subject to any disclaimer, the term of this patent is extended or adjusted under 35 U.S.C. 154(b) by 245 days.

(21) Appl. No.: 13/263,632

(22) PCT Filed: Apr. 9, 2010

(86) PCT No.: PCT/PL2010/000026
§ 371 (c)(1),
(2), (4) Date: Nov. 14, 2011

(87) PCT Pub. No.: WO2010/117287
PCT Pub. Date: Oct. 14, 2010

(65) Prior Publication Data
US 2012/0141425 A1 Jun. 7, 2012

(30) Foreign Application Priority Data
Apr. 10, 2009 (PL) .................................. 387780

(51) Int. Cl.
*A61K 38/14* (2006.01)
*A61K 35/76* (2006.01)
*A61P 35/00* (2006.01)
*C07K 14/075* (2006.01)
*C07K 17/06* (2006.01)

(52) U.S. Cl.
USPC ..... 514/1.2; 514/19.3; 514/20.9; 424/196.11; 424/499; 530/402; 435/235.1

(58) Field of Classification Search
None
See application file for complete search history.

(56) References Cited

U.S. PATENT DOCUMENTS
6,083,720 A * 7/2000 Chroboczek et al. ........ 435/69.1

FOREIGN PATENT DOCUMENTS
CA 2619278 A1 2/2007

OTHER PUBLICATIONS

Fender et al (Nature Biotechnology 15:52-56, 1997).*
Smith et al (International Journal of Oncology 17:841-50, 2000).*
Fuschiotti et al (Journal of General Virology 87:2901-1905, 2006).*
Goldmacher et al (Molecular Pharmacology 36:818-822, 1990).*
Medina-Kauwe et al (Gene Therapy 8:795-803, 2001).*
Zochowska et al (PLoS one 4(5) e5569, p. 1-12, May 2009) (in IDS).*
Zochowska, et al.; "Adenovirus Dodecahedron, as a Drug Delivery Vector"; PLoS ONE; May 1, 2009; Public Library of Science; United States.
Szolajska, et al.; "Development and use of the adenovirus dodecahedron for the intracellular delivery of therapeutic agents"; FEBS Journal; 31st Congress of the Federation-of-European-Biochemical-Societies (FEBS); Istanbul, Turkey; Jun. 24-29, 2006, Jun. 1, 2006; pp. 231-232; Blackwell Publishing; London, GB.

* cited by examiner

*Primary Examiner* — Mary E Mosher
(74) *Attorney, Agent, or Firm* — Christopher L. Parmelee; Walker & Jocke

(57) ABSTRACT

The embodiment of the invention is a virus-like particle vector, a process for the manufacture thereof, use of the virus-like particle vector and a pharmaceutical composition, which contains the virus-like particle vector. The vector is intended for the delivery of therapeutic agents into specific mammalian tissues, especially low molecular weight agents, in particular low molecular weight anti-cancer drugs into cancer tissues. More specifically, the invention relates to the virus-like particle vector, which constitutes an adenoviral dodecahedron with the therapeutic substance encapsulated or covalently linked.

17 Claims, 7 Drawing Sheets

Adenovirus

A

B

Dodecahedron

ADENOVIRUS DODECAHEDRON PARTICLES FOR DELIVERY OF PHARMACEUTICAL AGENTS

Adenoviruses (Ad) are medium-sized non-enveloped DNA viruses, which infect humans and animals. Two adenoviral capsid proteins are responsible for virus penetration at the beginning of infection. These include: trimeric fibre protein, responsible for virus attachment to the host cell surface, and pentameric penton base protein, involved in virion internalisation. These two proteins form a non-covalent complex called penton, presented schematically in FIG. 6.

As a result of overexpression of two penton proteins in the baculovirus system, symmetrical dodecahedric nanoparticles comprising 12 pentons form spontaneously. Simultaneously, dodecahedric virus-like particles, which comprises 12 penton base proteins only can be formed via a similar procedure. Both types of dodecahedra (Dd) retain the functionality of their constituents and show an extraordinary ability of cell penetration (Fender et al., 1997; Fender et al., 2003; Vivés et al., 2004).

The dodecahedron recognises two types of receptors. On one hand, while retaining the specificity of the penton base protein that recognises αv integrins, it shows affinity to the αv integrins, whose levels are elevated in newly grown vessels, which supply blood to the cancer tissue. At the same time, the dodecahedron has strong affinity to heparin sulphates (Vives et al., 2004), located at the surface of all epithelial cells.

Bleomycin (BLM) is a glycopeptide antibiotic used in the treatment of various types of cancers (Lazo and Sebti, 1999). The antibiotic acts by cleaving DNA in the cell nucleus, thus inhibiting cell division (Sausville et al., 1978; Carter et al., 1990). Bleomycin is exceptionally cytotoxic when located in the cell nucleus (Poddevin et al., 1991). However, the activity of the antibiotic is limited because, being hydrophilic, the particle has low penetration potential through cell membranes, has limited receptors on the plasma membrane and undergoes very quickly intracytoplasmic proteolysis (Mir et al., 1996; Lazo, 1996; Tounekti et al. 1993). Therefore, very high doses of the antibiotic are administered, which leads to serious adverse effects in the form of pulmonary fibrosis. Electroporation has been the method used heretofore to facilitate BLM penetration into the cancer tissue, which resultes in the increase of the anti-cancer effect of bleomycin (Gehl et al., 1998; Orlowski et al., 1988). Starting in 1991, clinical trials have been carried out using bleomycin electrochemotherapy in the treatment of cancers in humans (Gothelf et al., 2003). This applied mainly to cutaneous or subcutaneous tumours, but also to head and neck tumours. Bleomycin was administered directly into the tumour or intravenously, concomitantly with electric shock. Such therapies make it possible to stop tumour growth, inducing various levels of necrotic changes within the cancer tissue. Depending on the location of the tumour, partial or general anaesthesia, an additionally stressing procedure, was used during electroporation, In FR 2747681 (publ. 1997-10-24) and FR 2741087 (publ. 1997-05-16) a protein complex (adenoviral dodecahedron comprising the penton base protein and optionally containing the fibre protein) was disclosed. The adenoviral protein complex (A) contains: (a) 12 pentons (P), each of, which contains at least one penton base (Pb) and one fibre protein (F), wherein the pentons are linked through the Pb so that they form a dodecahedric structure resistant to proteolysis with a molecular weight of 4.8-6.6 MD, or (b) 12 Pbs form a dodecahedron as above, the molecular weight, however, is 3.2 to 4 MD. (A) does not contain any other adenoviral components and F and Pb are of the same or different adenoviral (Ad) serotypes.

In U.S. Pat. No. 6,083,720 (publ. (2000-07-04), EP0861329 (publ. 2000-07-04), WO 9718317 (publ. 2006-02-16) an adenoviral dodecahedron was claimed, being a protein complex, a composition containing such a complex and use thereof. A native or recombinant adenoviral protein complex is used in the treatment and prevention of human and animal diseases. The complex disclosed contains 12 pentons, wherein each contains at least one fibre protein and penton base protein, without any additional adenoviral elements, and the said fibre protein originates from one or more adenoviral serotypes, and the penton base proteins are linked with one another and form a stable dodecahedric structure resistant to proteolysis.

In patent application CA 2619278 (publ. 2007-02-02) a process for the encapsulation of therapeutic substances is provided. The invention concerns a composition, which comprises nanoparticles and use thereof for the encapsulation of therapeutically active substances inside nanoparticles having a specific coat. The particles are chemically formed so as to prevent high intracellular absorption. Encapsulation requires a direct bond between the nanoparticle and the therapeutically active substance. The pharmaceutical composition comprises nanoparticles with high affinity towards cancer cells and contains at least one therapeutic substance selected from a group comprising e.g. bleomycin.

Despite the aforementioned inventions, which focus on improved ways for the supply of therapeutic agents into the body, there is a continuing need to provide new, efficacious delivery therapies, using adenoviral dodecahedra.

The objective of this invention is development of conditions which, which would enable the use of a dodecahedric virus-like particle vector for therapeutic purposes and also preparation and characterisation of a pharmaceutical composition, which contains a vector carrying a low molecular weight therapeutic substance to be used in human therapy. The dodecahedron is a potentially polyvalent vector specific for cancer cells. The vector has adenoviral endosomolytic activity and, therefore, it penetrates into cellular cytosol easily. As discussed above, Dd has high affinity to αv integrins. The integrins recognise the RGD motif (arginine-glycine-aspartic acid). The adenoviral dodecahedron with 60 RGD motifs is probably the most specific ligand for αv integrins. As it is known that αv integrin levels are elevated in malignant tumour endothelium, the Applicant assumed that the Dd can selectively supply therapeutic agents inside endothelial cells from, which newly grown tumour blood vessels are formed. Therefore, the Applicant decided to use such virus-like particles for the transfer of low-molecular weight therapeutic agents, expecting that the use of a targeted therapeutic Dd conjugate would lead to increased bioavailability and limited adverse effects of low-molecular weight drugs, in particular anti-proliferation factors, in particular glycopeptides, including anti-cancer antibiotics, such as bleomycin.

The achievement of this objective and overcoming the issues stated in the art, related to the development of an invention, which enables the transfer of low-molecular weight therapeutic agents with increased bioavailability and reduced adverse effects of low-molecular weight drugs has been included in this invention.

In their work, the Applicants obtained recombinant dodecahedra (rDd) and demonstrated that dodecahedra penetrate cells with higher efficacy than the virus of origin, adenovirus serotype 3 (Ad3): rDds transduce 100% cells in cell cultures, and they have ability to transduce cells non-permissive for Ad3 as well. This results from the Dd gain-of-function, namely interaction with common components of cell membranes, heparin sulphate (HS) proteoglycans, not recognised by type 3 adenoviruses, from, which the Dd originates (Vives et al., 2004). HS interacts with positively charged protein fragments and it seems that such fragments are form in the Dd due to the proximity of penton base proteins in the VLP. Therefore, dodecahedron penetration occurs not only via viral receptors, but also through omnipresent heparin sulphates.

The recombinant dodecahedric particle (rDd) is obtained with high yield in insect cells in the baculovirus system. The yield is comparable to that described for the most efficient bacterial protein expression systems, being 10 mg rDd per 100 mL of cell culture. rDds have been heretofore purified by sucrose gradient ultracentrifugation. This enables elimination of cellular proteins, but fails to do so with nucleic acids, most likely attached to the VLP surface.

The present invention relates to a polyvalent virus-like particle vector, characterised in that it constitutes a recombinant adenoviral dodecahedron particle comprising adenoviral pentons or adenoviral penton base proteins, with an encapsulated or covalently linked low-molecular weight therapeutic substance in at least two copies, wherein the therapeutic substance is an anti-proliferative agent, preferably an anti-cancer agent, wherein the adenoviral dodecahedron originates from a mammalian, especially human, virus. Preferably, the delivered low-molecular weight therapeutic substance is an anti-proliferative agent, preferably a glycopeptide, in particular an anti-cancer agent, preferably belonging to the bleomycin family, according to Formula I,

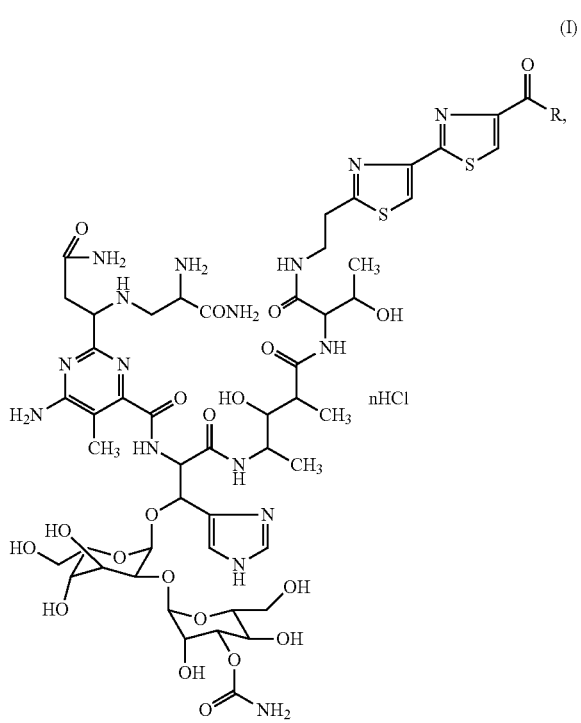

preferably bleomycin A5, according to Formula II.

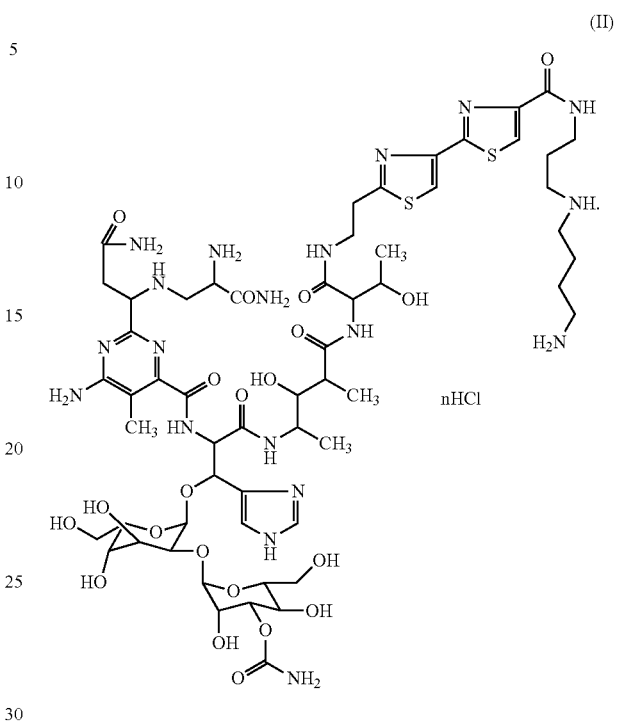

The low-molecular weight therapeutic substance is preferably encapsulated in or linked to the polyvalent recombinant adenoviral dodecahedron particle by cross-linking with a homo- or heterobifunctional chemical compound, preferably using carbodiimide (EDC), to amine groups or cysteine residues of the dodecahedron or else at the N-terminus or C-terminus of the penton base protein in the dodecahedron.

Preferably, in the dodecahedron-bleomycin (Dd-BLM) conjugate, the penton base protein monomer carries between 0 and 2 BLM particles, with significant majority of monomers containing one BLM molecule, preferably one Dd molecule containing 60 base protein monomers carries at least 30 BLM residues.

Preferably, the linked or encapsulated low-molecular therapeutic substance is an unstable drug, such as anti-cancer drugs (medicine is art of healing—Wikipedia), preferably bleomycin, drug against neurodegenerative diseases, preferably 3,4-dihydroxyphenyl-1-alanine (L-DOPA), drug against tuberculosis and intercellular parasites, preferably isoniazid, anti-asthmatic agents, preferably salbutamol, intravenous anaesthetic agents, preferably thiopental, drugs against pathogenic organisms, preferably drugs against toxoplasmosis, leishmaniasis, trypanosomiasis and rickettsiosis.

Preferably, the adenoviral dodecahedron carries the low-molecular weight therapeutic substance that is unstable at storage or in mammalian serum or else in the presence of intracellular eukaryotic enzymes.

Preferably, the linkage of the low-molecular weight therapeutic substance with the adenoviral dodecahedron ensures increased bioavailability of the therapeutic substances, in particular drugs against pathogenic organisms.

Preferably, the linkage of the low-molecular weight therapeutic substance with the adenoviral dodecahedron ensures increased bioavailability of the therapeutic substances, in particular therapeutic substances responsible for serious adverse effects.

Preferably, the cytotoxically effective BLM concentration delivered with the Dd is at least 50 times as low as in the case of free bleomycin.

Another subject embodiment of the invention is a process for the manufacture of a virus-like particle vector, characterised in that the recombinant adenoviral dodecahedron particle originates from a mammalian, especially human, virus, and that it is produced in insect cells and, subsequently, it is purified using ultracentrifugation in sucrose concentration gradient and, subsequently, on an ion-exchange column, thus obtaining a fraction of pure rDds and, subsequently, to the resulting recombinant adenoviral dodecahedron comprising pentons or penton base proteins, at least two copies of the low-molecular weight therapeutic substance are encapsulated or attached covalently by chemical cross-linking, wherein the therapeutic substance is an anti-proliferation agent, preferably an anti-cancer drug.

Preferably, the low-molecular weight therapeutic substance is an anti-proliferation agent, preferably a glycopeptide, in particular an anti-cancer drug, preferably belonging to the bleomycin family according to Formula I, preferably bleomycin A5 according to Formula II.

Preferably, the attached low-molecular weight therapeutic substance is placed through encapsulation inside the vector or attached by chemical cross-linking on the vector surface with a homo- or heterobifunctional chemical compound, preferably using carbodiimide (EDC).

Preferably the low-molecular weight therapeutic substance is attached to amine groups or cysteine residues of the dodecahedron or else at the N-terminus or C-terminus of the penton base protein in the dodecahedron.

Another embodiment of the invention is use of the virus-like particle vector, which is a recombinant adenoviral dodecahedron, constituting a conjugate of the recombinant adenoviral dodecahedron particle formed from pentons or penton base proteins, with at least two copies of an encapsulated or covalently linked low-molecular weight therapeutic substance, wherein the therapeutic substance is an anti-proliferative agent, preferably an anti-cancer drug, wherein the adenoviral dodecahedron originates from a mammalian, especially human, virus for the delivery of therapeutic agents into tissues, preferably for the delivery of low-molecular weight therapeutic substances, preferably anti-cancer agents, into mammalian cancer tissues.

Preferably, the attached low-molecular weight therapeutic substance is an anti-proliferation agent, preferably a glycopeptide, in particular an anti-cancer drug, preferably belonging to the bleomycin family according to Formula I,

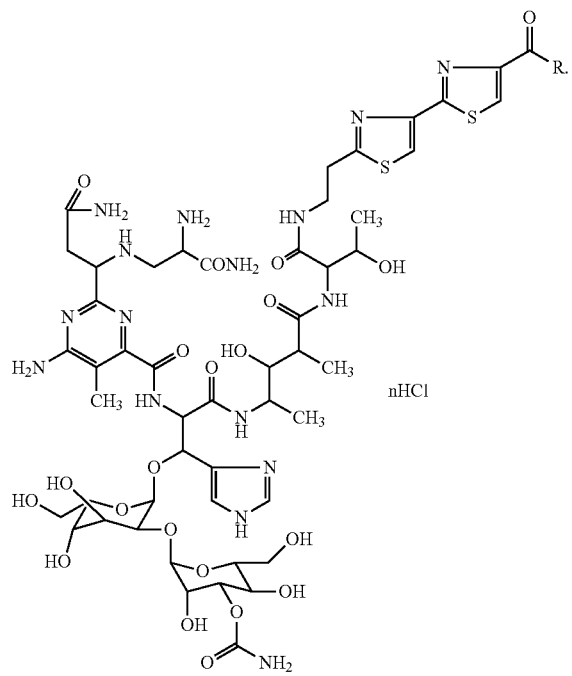

preferably bleomycin A5, according to Formula II

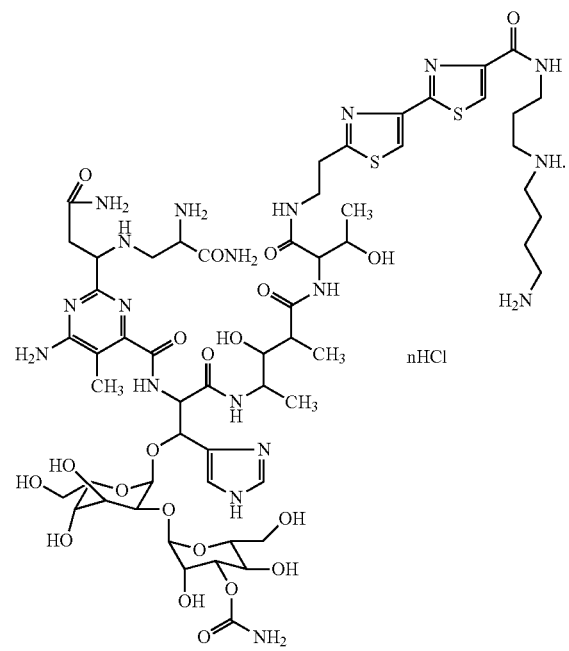

Preferably, at least two copies of the low-molecular weight therapeutic agent are encapsulated or linked to the recombinant adenoviral dodecahedron particle by cross-linking with a homo- or heterobifunctional chemical compound, preferably using carbodiimide (EDC), attached to amine groups or cysteine residues of the dodecahedron or else at the N-terminus or C-terminus of the penton base protein in the dodecahedron.

Preferably, in the dodecahedron-bleomycin (Dd-BLM) conjugate, the penton base protein monomer carries between 0 and 2 BLM particles, with significant majority of monomers carrying one BLM molecule, preferably one Dd molecule in the conjugate containing 60 base protein monomers carries at least 30 BLM residues.

Preferably, the transferred low-molecular therapeutic substance is an unstable drug, such as anti-cancer agents, preferably bleomycins, drugs against neurodegenerative diseases, preferably 3,4-dihydroxyphenyl-1-alanine (L-DOPA), drugs against tuberculosis and intercellular parasites, preferably isoniazid, anti-asthmatic agents, preferably salbutamol, intravenous anaesthetic agents, preferably thiopental, drugs against pathogenic organisms, preferably drugs against toxoplasmosis, amoebiasis, leishmaniasis, trypanosomiasis and rickettsiosis.

Preferably, the transferred therapeutic substance is unstable at storage, in mammalian serum or else in the presence of intracellular eukaryotic enzymes.

Preferably, the linkage of the low-molecular weight therapeutic substance with the adenoviral dodecahedron ensures increased bioavailability of the therapeutic agents, in particular therapeutics against pathogenic organisms.

Preferably, the linkage of the low-molecular weight therapeutic substance with the adenoviral dodecahedron ensures increased bioavailability of the therapeutic substances, in particular therapeutic substances responsible for serious adverse effects.

Preferably, the effective cytotoxic BLM concentration delivered with the Dd is at least 50 times as low as in the case of free bleomycin.

Another embodiment of the present invention is a pharmaceutical composition, characterised in that it contains a recombinant polyvalent adenoviral dodecahedron particle formed from pentons or penton base proteins, which carries at least two copies of the low-molecular weight therapeutic substance, wherein the therapeutic substance is an anti-proliferation agent, preferably an anti-cancer agent, wherein the adenoviral dodecahedron originates from a mammalian, especially human, virus.

Preferably, the transferred low-molecular weight therapeutic substance is an anti-proliferation agent, preferably a glycopeptide, in particular an anti-cancer drug, preferably belonging to the bleomycin family, according to Formula I,

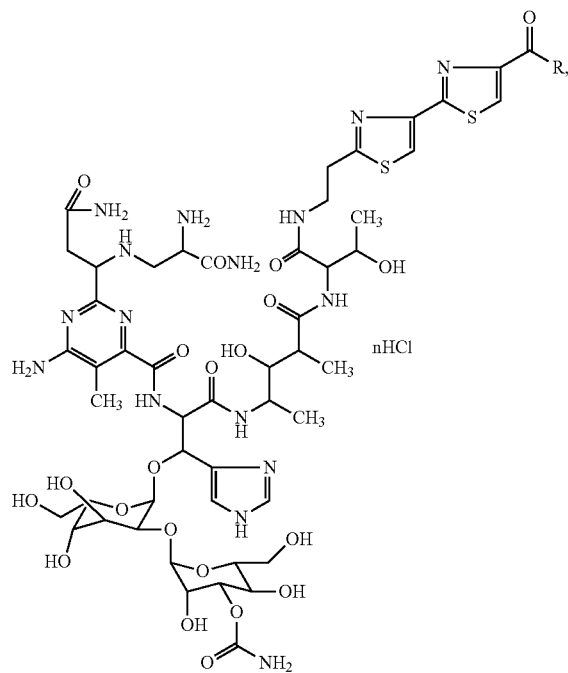

preferably bleomycin A5, according to Formula II

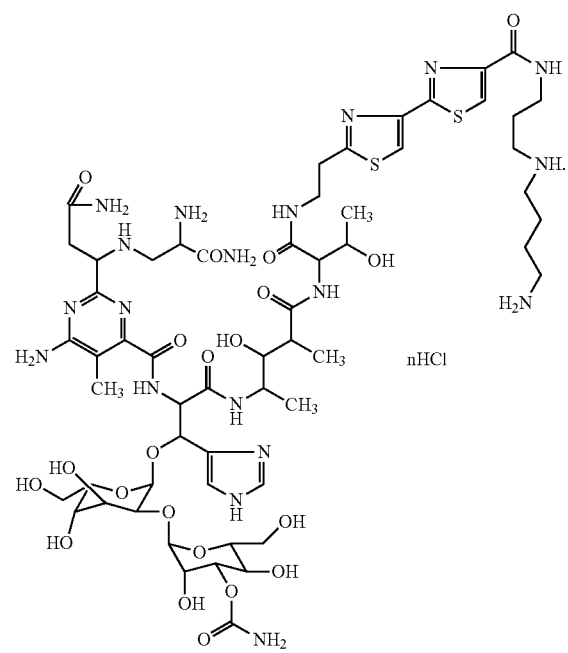

Preferably, at least two copies of the low-molecular weight therapeutic substance are encapsulated or linked to the recombinant adenoviral dodecahedron by cross-linking with a homo- or heterobifunctional chemical compound, preferably using carbodiimide (EDC), to amine groups or cysteine residues of the dodecahedron or else at the N-terminus or C-terminus of the penton base protein in the dodecahedron.

Preferably, in the dodecahedron-bleomycin (Dd-BLM) conjugate, the penton base protein monomer carries between 0 and 2 BLM particles, with significant majority of monomers containing one BLM molecule, preferably one Dd molecule containing 60 base protein monomers carries at least 30 BLM residues.

Preferably, the attached low-molecular therapeutic substance is an unstable molecule, such as anti-cancer drugs, preferably bleomycins, agents against neurodegenerative diseases, preferably 3,4-dihydroxyphenyl-1-alanine (L-DOPA), drugs against tuberculosis and intercellular parasites, preferably isoniazid, anti-asthmatic agents, preferably salbutamol, intravenous anaesthetic drugs, preferably thiopental, drugs against pathogenic organisms, preferably drugs against toxoplasmosis, amoebiasis, leishmaniasis, trypanosomiasis and rickettsiosis.

Preferably, the adenoviral dodecahedron delivers the low-molecular weight therapeutic substance, unstable in the free form at storage or in mammalian serum or else in the presence of intracellular eukaryotic enzymes.

Preferably, the attachment of the low-molecular weight therapeutic substance to the adenoviral dodecahedron ensures increased bioavailability of the therapeutic substances, in particular drugs against pathogenic organisms.

Preferably, the attachment of the low-molecular weight therapeutic substance to the adenoviral dodecahedron ensures increased bioavailability of the therapeutic substances, in particular therapeutic substances responsible for serious adverse effects.

Preferably, the Dd-BLM conjugate inhibits the proliferation of cancer cells. Preferably, the effective cytotoxic BLM concentration delivered with the Dd is at least 50 times as low as that of free bleomycin.

BRIEF DESCRIPTION OF DRAWING FIGURES

FIG. 1 shows a scheme of the adenovirus, penton and two dodecahedra (Dd).

FIG. 2 shows Dd stability analysed using dynamic light scattering (DLS) technique.

FIG. 3 shows Dd stability during lyophilisation, inside HeLa cells and in human serum, as well as Dd reconstitution from free penton base (Pb) proteins.

FIG. 4 shows the cytotoxicity of bleomycin delivered by the Dd.

FIG. 5 shows the effect of Dd-BLM activity on HeLa cells.

FIG. 6 schematically shows two proteins that form a non-covalent complex called penton.

DETAILED DESCRIPTION

The figures enclosed facilitate better explanation of the nature of the invention.

Figure 1:
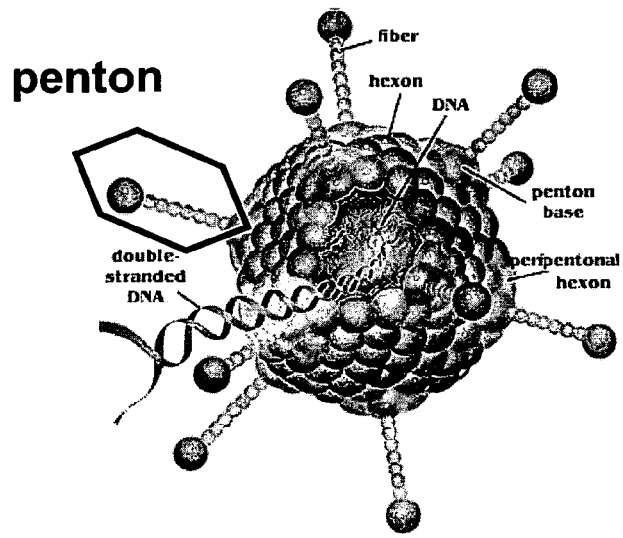
FIG. 1 (A, B) shows a scheme of the adenovirus, penton and two dodecahedra (Dd).
Figure 1:
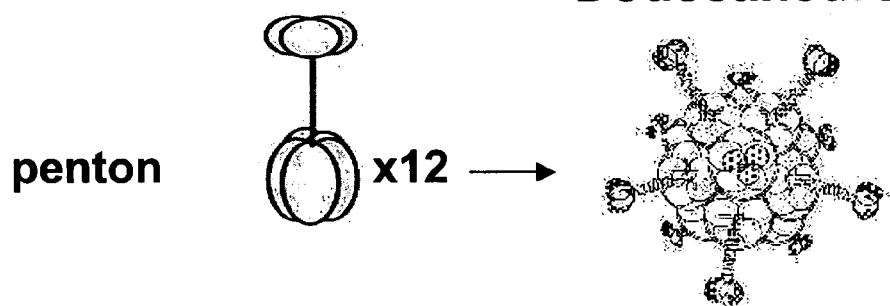
Figure 1:
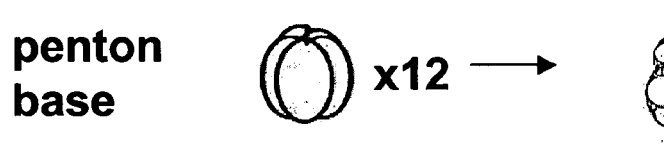

Examples illustrating the invention defined above are shown below.

The applicants initiated own research concerning the adenoviral dodecahedron. The research related to overexpression, purification and characterisation of dodecahedra and also their application for intracellular delivery of low-molecular weight drugs by chemical conjugation with a vector. The research included:

Preparation of high-quality preparations of dodecahedra purified to achieve a homogeneity. The resulting preparations are devoid of proteins, nucleic acids and proteases from cells, in which Dd overexpression occurs.

Testing vector stability conditions. It was proved that factors such as pH, ionic strength and temperature, affect Dd integrity. Borderline conditions were developed for the storage, shipment and use of Dd preparations in various conditions, suggesting possible use under tropical conditions.

Testing conditions of Dd reconstitution from free penton base proteins. Biophysical conditions were developed in order to obtain a dodecahedric vector in vitro from its free constituents, for the possible encapsulation of low-molecular weight therapeutic agents.

Construction of a dodecahedron (Dd) conjugate with a low-molecular weight therapeutic agent, especially such as bleomycin (BLM), by covalent linkage of the therapeutic agent with the dodecahedric vector.

Use of the Dd-BLM conjugate in tissue cultures and demonstration of remarkable improvement in conjugate bioavailability with respect to free bleomycin.

It appeared that the virus-like particle vector developed according to the invention made it possible to achieve better penetration of hydrophilic anti-proliferation therapeutic agents, especially glycopeptides, such as anti-cancer antibiotics, in particular such as bleomycin, through cell membranes. The use of the Dd for the delivery of therapeutic agents most likely means at the same time specific targeting of such agents to newly grown blood vessels, which supply nutrients to neoplastic tumours. It is known that the RGD motif interacts with αv integrins whose levels are elevated only in the endothelial cells, which constitute newly grown vessels, which supply blood to the cancer tissue (Chen, 2006). The motif is located in the penton base protein of, which the Dd is composed; therefore, the Dd, which contains 60 RGD motifs is a highly specific ligand for αv integrins and, simultaneously, it has strong ability to penetrate cells owing to its endoosmolytic activity and affinity to heparin sulphates.

EXAMPLES

Use of Dd as a Vector for the Delivery of Bleomycin (BLM) Antibiotic, a Low-Molecular Weight Therapeutic Agent The biological (cytotoxic) effect of a Dd-BLM preparation, which carried numerous antibiotic copies was tested on human cancer cells in in vitro cultures. It appeared that the chemical cross-linking reaction between the vector and BLM did not reduce its cell penetration ability. Furthermore, the antibiotic's cytotoxic activity was retained. Namely, Dd-BLM, when penetrating into human HeLa cells in in vitro cultures, degrades nuclear DNA, similarly to free bleomycin.

It was proved that the cytotoxically effective concentration of the antibiotic delivered with the Dd was approx. 100-fold lower than that used with free BLM. More than 60% human cancer cells (HeLa) in in vitro cultures were destroyed after the administration of the Dd-BLM conjugate, which was proved using the MTT cytotoxicity test (FIG. 4C). The cytotoxic effects were not observed either in the case of dodecahedron or free bleomycin administration in doses equivalent to those carried by the Dd-BLM conjugate.

Dd-BLM efficiently penetrates through cell membranes using receptors recognised by either Dd or BLM. Most likely, the vector undergoes gradual proteolysis in the cytoplasm of human HeLa cells, as a result of, which peptides are released with attached bleomycin, wherein the BLM-peptides penetrate into the nucleus in, which the antibiotic, bleomycin in this case, is active.

The cytotoxic BLM activity is known to result from DNA damage. Phosphorylation of the C-terminal region of the H2AX histone in higher eukaryotic cells is one of chromatin modifications in response to double-strand DNA breaks. A specific antibody, which recognises the phosphorylated H2AX histone form was used as the probe for detecting DNA damage. Dd-BLM, when penetrating into human cancer cells in in vitro cultures, degrades nuclear DNA, similarly to free bleomycin.

In the process of the invention, Dd, being a recombinant protein (rDd), is obtained with extremely high yield in insect cells in the baculovirus system. The overexpression is 10 mg of rDd per 100 mL of cell suspension. This overexpression yield is comparable to that achieved in the most efficient bacterial systems (Song et al., 2008). rDds have been heretofore purified by saccharose gradient ultracentrifugation. The stage made it possible to eliminate low- and medium-molecular weight cell proteins, but failed to do so with nucleic acids, most likely attached to the rDd surface. Due to the planned therapeutic use of the Dd, it was needed to prepare a better purified and more homogeneous product, achieved owing to a 2-stage protein purification process. After initial Dd purification in saccharose gradient, ion-exchange chromatography was used. A pure rDd fraction was obtained (more than 95% purity), confirmed in product analysis using electrophoresis technique in polyacrylamide gels and using electron microscopy.

Figure 2:
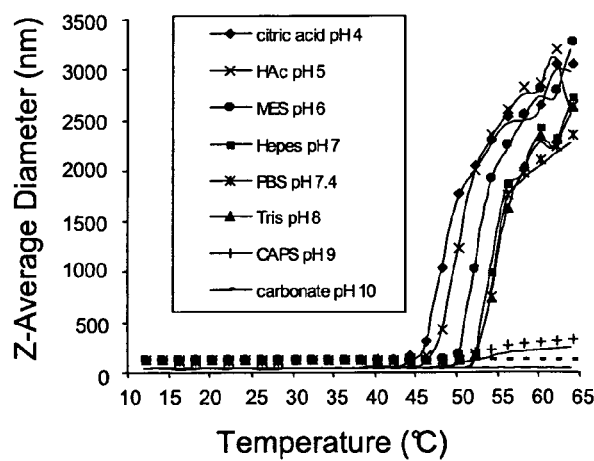
FIG. 2 shows Dd stability analysed using dynamic light scattering (DLS) technique. Dd thermal stability depending on pH and ionic strength. (A) Dd in 150 mM NaCl was tested using DLS technique at various pH values at temperature increments of 2° C. every 2 min between 12 and 65° C. (B) Electrophoresis analysis of Dd and pentameric bases (Pb) in CAPS buffer (pH 9) and in carbonate buffer (pH 10). Some samples were subjected to temperature changes simulating DLS conditions (marked with DLS). (C) DLS analysis carried out using Dd samples in PBS in various ionic strength conditions. Average values from 3 apparatus readings are shown.
Figure 2:
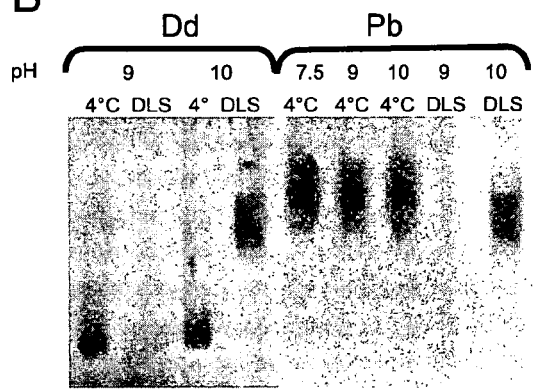
Figure 2:
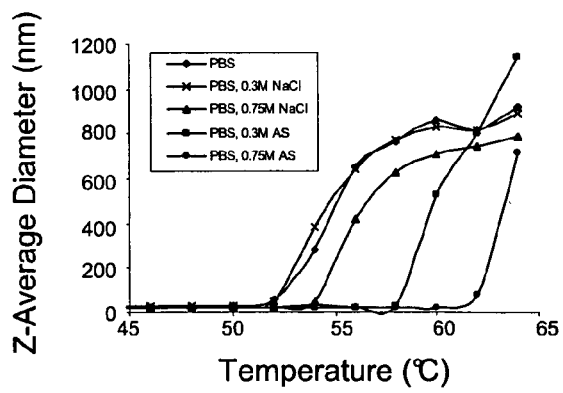
Figure 3:
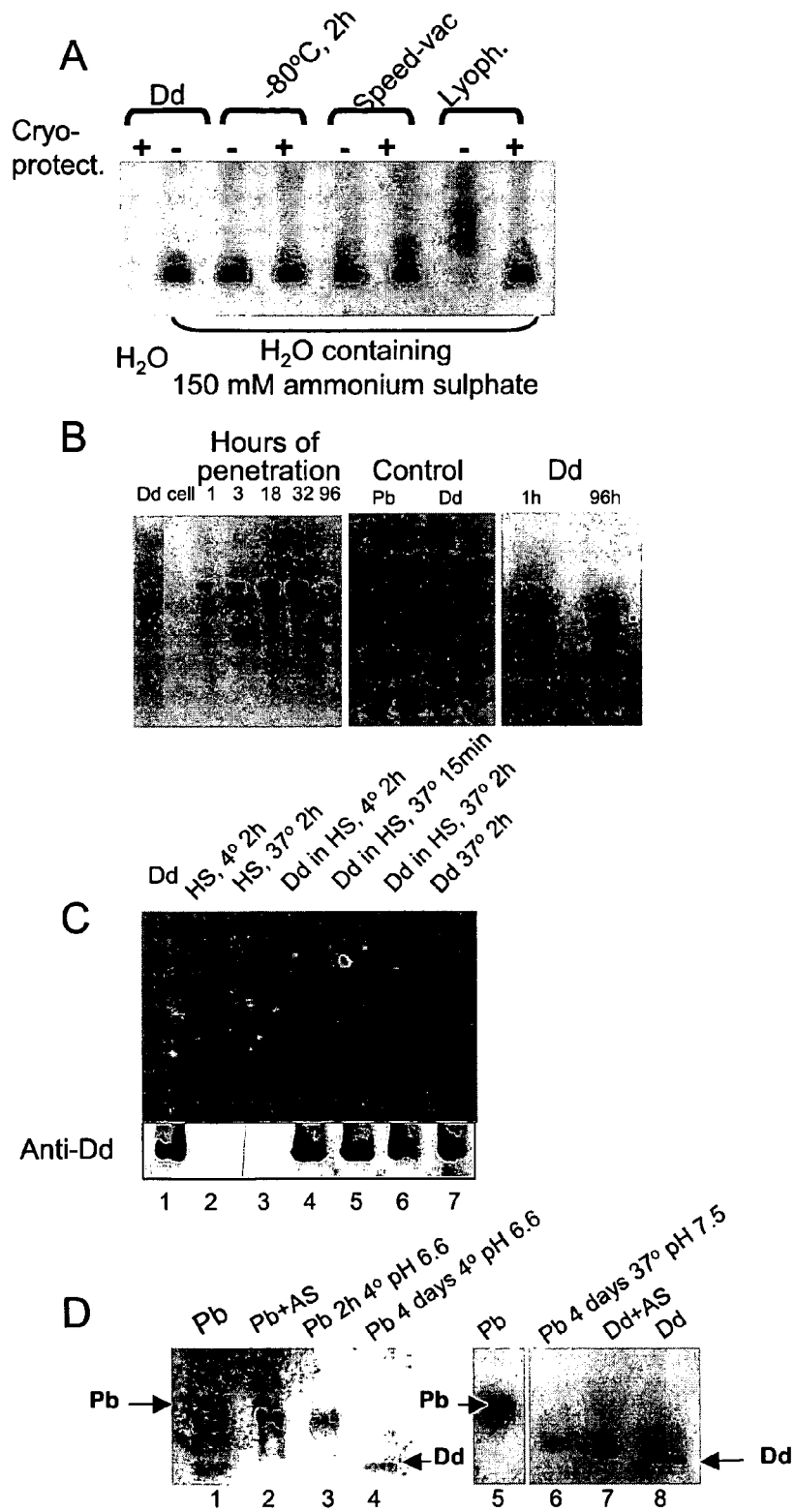
FIG. 3 shows Dd stability during lyophilisation, inside HeLa cells and in human serum, as well as Dd reconstitution from free penton base (Pb) proteins. (A) Purified Dds were dialysed overnight at 4° C. against water or 150 mM aqueous ammonium sulphate. Mannitol (0.4%) and sucrose (0.4%) were added to the samples marked "cryoprotectant +". Dd samples were frozen at −80° C. or dried with speed-vac or freeze-dried. The dried samples were reconstituted in the initial water volume. The samples were centrifuged for 30 min at 13000 rpm, and the condition of proteins in the supernatant was analysed using agarose gel electrophoresis. (B) Dd stability in the HeLa cell culture. Purified Dd samples (2 µg/100 µL) were applied onto $2 \times 10^4$ portions of HeLa cells. After specified penetration times, cell lysates were isolated and were separated on polyacrylamide gel under denaturing conditions (left-hand panel) or on agarose gel under non-denaturing conditions (two right-hand panels). In both cases Western-blot analysis was carried out using anti-Dd antibodies. Control Dd samples contained 30 ng of protein, and the samples of pentameric bases (Pb) contained 10 ng of protein. (C) Dd stability in human serum. Dd samples (5 µg aliquots) concentrated by ultrafiltration in Microcon (Millipore) were incubated in human serum (HS) at a temperature of 4° C. for 2 hours (lane 4) or at 37° C. for 15 min or 2 hours (lanes 5 and 6, respectively). The samples were separated on agarose gel under non-denaturing conditions and, subsequently, analysed by Western blot using a Dd-recognising antibody. The upper part is a Coomassie-stained gel with proteins remained after the transfer, and the bottom part is the developed Western blot. Lanes 1 and 7 correspond to Dd samples without serum, non-treated or incubated for 2 hours at 37° C., respectively. Lanes 2 and 3 correspond to human serum incubated for 2 hours at 4 or 37° C., respectively. (D) Purified Pbs were dialysed either at 4° C. against 50 mM phosphate buffer, pH 6.6, containing 750 mM ammonium sulphate (left-hand panel), or at a temperature of 37° C. against 100 mM phosphate buffer, pH 7.5 (right-hand panel). The samples were centrifuged for 30 min at 13000 rpm, and the proteins in the supernatant were analysed using agarose gel electrophoresis under non-denaturing conditions. Lane 1 contains the starting Pb preparation used for Dd reconstitution; lane 2 corresponds to free Pbs with 750 mM ammonium sulphate added before reconstitution; lane 3 contains free pentameric bases after 2-hour dialysis (two dialysis buffer changes). Lanes 4 and 6 correspond to Dd reconstructed during 4-day dialysis at 4 and 37° C., respectively. Lanes 7 and 8 correspond to Dd, and sample 8 contains 750 mM ammonium sulphate added before reconstruction.

The biochemical and biophysical tests conducted (electron microscopy, agarose gel electrophoresis in agarose gel in non-denaturing conditions and in polyacrylamide gels in denaturing conditions and measurements using dynamic light scattering (DLS)) proved the rDd to be stable up to 40° C. in a wide pH range and up to approx. 50° C. at a pH of 7-8, at physiological NaCl concentration (150 mM). It was shown that high ionic strength conditions largely stabilise its structure, because the rDd is then not denatured up to a temperature of 60° C. (FIG. 2). The vector particle retains integrity during dialysis, after freezing and thawing, in speed-vac drying and during freeze-drying in the presence of a cryoprotectant (FIG. 3A). The high vector stability makes rDd handling and storage easier. Furthermore, the rDd was found to retain integrity in conditions, which simulate its in vivo use; namely, it was stable in human serum at a temperature of 37° C. for at least 2 hours (FIG. 3B). The results make it possible to use the rDd as a vector for various applications and in various environmental conditions.

The analysis carried out using mass spectrometry techniques proved that in the dodecahedron conjugate with the anti-cancer antibiotic prepared by the Applicant, one virus-like particle carries 60 drug molecules on average (FIG. 4A), which confirms the multivalency of the vector used. Apart from attachment to the vector surface, increased bioavailability of low-molecular weight compounds may be achieved by their encapsulation inside the virus-like particle. The Applicants developed conditions in, which dodecahedra associated from their constituents, being pentameric bases (FIG. 3D). Owing to dodecahedron in vitro reconstruction in the presence of low-molecular weight compounds, it is possible to obtain a virus-like particle, which contains an encapsulated therapeutic substance.

According to the Applicant, the properties of the Dd discussed above imply the potential of the nanoparticle to be used as a vector for the delivery of therapeutic agents to human tissues. The first example concerns bleomycin, an anti-cancer antibiotic.

The Applicant found that bioavailability of the antibiotic increased owing to the use of the Dd as the vector; this should enable the use of reduced doses and, in consequence, reduce adverse effects of its activity. After the stage of tests carried out in tissue cultures, studies in the mouse cancer model will be conducted. If the Dd-BLM preparation used in the model system, such as mice with implanted human brain tumour, proves at least as efficacious as BLM delivery by electrochemotherapy used previously, this will make it possible to suggest using the Dd-BLM conjugate in human anti-cancer treatment. Therefore, the use of bleomycin in anti-cancer treatment could be limited to the administration of a Dd-BLM preparation without any need to use electric shock, which frequently requires complete anaesthesia.

Example I

A Process for the Preparation of the Adenoviral Dodecahedron

Due to the planned therapeutic use of the rDd, it was needed to prepare a better purified and more homogeneous product, achieved owing to the addition of the second protein purification stage to the previous protocol; after initial rDd purification in sucrose gradient, low-pressure ion-exchange chromatography was used, which yielded a pure rDd fraction.

For Dd expression, a recombinant baculovirus, which comprised the penton base protein gene of the human serotype 3 adenovirus (Ad3) was used (Fender et al., 1997). The amplification of the recombinant baculovirus carrying the base protein gene was carried out in a monolayer cell culture of *Spodoptera frugiperda* (Sf21). The cells were cultured in TC100 medium containing 5% foetal bovine serum (Invitrogen). The recombinant Dd was overexpressed in *Trichoplusia ni* cells (also known as High Five, HF), cultured in suspension in the Express Five SFM (Invitrogen) medium in the presence of gentamycin (50 mg/L) and amphotericin B (0.25 mg/L). *Trichoplusia ni* cells were infected with the recombinant baculovirus at the MOI (multiplicity of infection) of 4 infectious units per one cell. 48 hours after the infection, the cells were harvested and lysed by freezing and thawing three times. The supernatant obtained after lysate clarification was centrifuged in 15-40% sucrose gradient (Fender at al., 1997). The VLP product, recovered in 30-40% sucrose, was contaminated with cellular proteins and nucleic acids. Final Dd purification was achieved by chromatography on an ion-exchange column as a result of, which dodecahedra were prepared as a homogeneous fraction. The oligomeric status of the particles and purity level of the resulting product were analysed in native agarose gels, using electron microscopy and in denaturing polyacrylamide gels.

Example II

Testing the Life and Stability of the Adenoviral Dodecahedron

The stability and solubility of purified Dd particles was tested. To this end, the purified rDds were dialysed against various buffers (with 3 changes of each) and, subsequently, incubated at 30 or 37° C. After incubation, the samples were centrifuged and proteins in the supernatant were analysed using agarose gel electrophoresis. The Dd remains dissolved at 4° C. and pH of 4.0 to 10.9, in the presence of 150 mM NaCl. Without NaCl, the Dd does not remain in solution and it disappears from the supernatant during centrifugation. Therefore, NaCl in physiological concentration protects Dds against denaturation.

In order to test Dd resistance to thermal denaturation, dynamic light scattering (DLS) technique was used owing to, which protein denaturation or aggregation can be monitored. Protein samples (0.2 mg/mL) were dialysed against suitable buffers and filtered though filters with 0.45 μm pore size in order to remove any dust particles. The samples were placed in a cuvette (45 μL, Greiner, Frickenhausen, Germany) and automated particle size measurements were carried out using ZS Nano Zetasizer apparatus (Malvern, Worcestershire, GB). The temperature gradient was 2° C. every 2 min between 12 and 65° C. The data were evaluated using a cumulative method.

In a pH of 4 to 9, the size of dodecahedric particles was constant up to 40° C. (FIG. 2A). Above this temperature, particle sizes increased exponentially with increasing temperatures, which indicated denaturation and aggregation. Dd denaturation/aggregation starts at a pH of 4-5 at a temperature lower by about 10° C. than at pH 7-8. At pH 9 (CAPS buffer) and 10 (carbonate buffer), small particle size changes occur. Protein analysis in native agarose gels proved at a pH of 10 that the Dd dissociates into free pentameric bases and at pH 9 (CAPS buffer) the protein disappears, most likely due to aggregation (FIG. 2B). It is noted that CAPS is an organic buffer, which may cause aggregation by interacting with surface hydrophobic fragments. The addition of 750 mM NaCl to PBS leads to increased Dd melting temperature ($T_m$), which indicates structural stabilisation (FIG. 2C). However, the most significant $T_m$ value increase was due to the addition of ammonium sulphate and led to a positive shift of about 12° C. (FIG. 2C).

The tests completed proved that the vector particle retains integrity during dialysis, after freezing and thawing and in speed-vac drying in the presence of 150 mM ammonium sulphate. A cryoprotectant is required during lyophilisation in order to preserve Dd structure (FIG. 3A). Vector life in cell cultures was tested in HeLa cells at various time points after Dd addition. Purified Dd (4 μg/100 μL, 10.8 nM) was applied to HeLa cells in 24-well plates ($2 \times 10^4$ cells/well), in the FBS-free medium. The cells were incubated in an incubator at 37° C. Three hours after Dd addition, FBS was added to the medium to a final concentration of 10%. The cells were harvested at specified time points (FIG. 3B) and lysed in the hypotonic buffer. Samples corresponding to half the cells were analysed in polyacrylamide gel in denaturing conditions (SDS-PAGE) and the other half was analysed in agarose gel in non-denaturing conditions and, subsequently, analysed in both cases by Western blot using anti-Dd antibodies.

The quantity of intracellular Dds increased up to 32 hours following transduction. Simultaneously, partial Dd proteolysis occurred, due to, which only part of the base protein remained in the cells after 4 days (FIG. 3B, left-hand panel).

Analysis in native agarose gel proved that 96 hours after penetration most of the intracellular vector migrated between Dd and pentameric bases (Pb), which indicated removal of external Dd loops with retained molecule integrity (FIG. 3B, right-hand panel).

Dd Stability During Incubation in Human Serum

Dd samples (5 μg liquots) concentrated by ultrafiltration in Microcon (Millipore), were incubated in human serum (SL) at a temperature of 4° C. for 2 hours and at 37° C. for 15 min or 2 hours. The Dd retains integrity in conditions, which simulate its potential in vivo use; namely, it is stable in freshly prepared human serum at a temperature of 37° C. for at least two hours (FIG. 3C).

Example III

Reconstruction of Dodecahedra from their Constituent Parts (Pentameric Bases)

A homogeneous fraction of free pentameric bases (Pb) was obtained during purification on an ion-exchange column. The purified rPbs were dialysed against 50 mM pH 6.6 or pH 7.5 phosphate buffers containing 750 mM ammonium sulphate with several buffer changes. After the end of dialysis, the samples were centrifuged and the oligomeric status of proteins in the supernatant was analysed using agarose gel electrophoresis. In high ionic strength conditions during 4-day dialysis at a temperature of 4° C. or 37° C., association of dodecahedra from pentameric bases occurs. Owing to dodecahedron in vitro reconstruction from their constituent parts in the presence of low-molecular weight compounds, it is possible to obtain a vector, which contains a therapeutic substance encapsulated in the virus-like particle.

The results provided indicate that the Dd can be conveniently stored and transported and reconstructed in vitro from its constituents; this proves that it can be used for various therapeutic purposes, in various configurations and in various environmental conditions.

Example IV

A Process for the Preparation of the Vadenoviral Dodecahedron Particle with Bleomycin Bleomycin $A_5$ hydrochloride (Hangzhou Xiangyuan Co., Ltd., China) was chemically attached to previously purified rDd particles during a two-stage conjugation procedure using carbodiimide (EDC) and succinic acid ester (s-NHS) (Pierce, Rockford Ill., USA). Dodecahedra at a concentration of 27 nM were activated in the 0.1 M pH 6.0 MES buffer containing 0.5 M NaCl, in the presence of 0.31 mM EDC and 5 mM s-NHS. Conjugation with bleomycin (23 mM) was carried out for two hours at room temperature upon gentle stirring. The reaction was terminated by adding hydroxylamine to a final concentration of 10 mM. The reagents used and unbound bleomycin were eliminated during 24-hour dialysis with four changes of 20 mM pH 7.5 Tris buffer containing 150 mM NaCl and 5% glycerol.

Bleomycin quantity attached to the Dd was determined using mass spectrometry technique. The analysis was carried out using a Perseptive Biosystems mass spectrometer (Framingham, Mass.), by way of a pulse nitrogen laser at a wavelength of 337 nm. The samples were concentrated in ZipTipC4 (Millipore) and extracted with saturated sinapinic acid solution prepared in 80% mixture of aqueous acetonitrile (vol./vol.) comprising 0.3% trifluoroacetic acid according to the manufacturer's instructions. The eluent mixture was transferred onto a steel plate and dried on air. The apparatus was calibrated using bovine albumin (Biosystems) with a molecular weight of 66431 Da.

In the Dd-BLM conjugate, the penton base protein monomer (of, which Dd comprises) carries between 0 and two BLM particles (the BLM molecular weight is 1400) with significant majority of monomers containing one BLM molecule (FIG. 4A). The data indicate that one Dd molecule, which contains 60 base protein monomers carries 60 BLM residues on average. Tests using dynamic light scattering technique (DLS) proved that the melting temperature of the Dd-BLM conjugate is very similar to that of the initial dodecahedron, which indicates that the cross-linking reaction does not change the biophysical properties of the vector. The results of the studies underscore vector polyvalency, wherein one Dd particle is able to provide multiple copies of the therapeutic substance.

Example V

Biological Assay of the Adenoviral Dodecahedron Particle with Bleomycin

HeLa human cancer cells were treated with the Dd-BLM conjugate prepared according to the invention. Similarly to free bleomycin, the Dd-BLM conjugate led to the inhibition of cancer cell proliferation. What was the most important, the cytotoxically effective BLM concentration delivered with the Dd was 100 times as low as in the case of free bleomycin.

The cytotoxic Dd-BLM activity was quantitatively evaluated in vitro using the MTT test (MTT, 3-(4,5-dimethylthiazol-2-yl)-2,5-diphenyltetrazolium bromide). In the test, the ability of live cells to reduce the soluble yellow tetrazolium salt (MTT) to blue formazan crystals is used. HeLa cells cultured in 96-well plates ($10^4$ cells/well) were incubated for 3 hours at 37° C. in 100 μL of the EMEM medium containing a) various quantities of Dd (1 μg corresponds to 2.7 nM), b) Dd-BLM (1 μg corresponds to 2.7 nM Dd and 0.08 μM BLM) or c) free bleomycin (0.13, 1 and 8 μM, respectively). After 3 hours, foetal bovine serum was added to a final concentration of 10%. After various incubation times at 37° C., the incubation medium was removed and 100 μL EMEM containing 0.5 mg/mL MTT (Sigma) was added. The plates were incubated according to the manufacturer's instructions; optical density measurements were carried out using an HTi reader (Biotek, VT Winooski, USA). The number of live cells was calculated according to the protocol (Mosmann, 1983).

Figure 4:
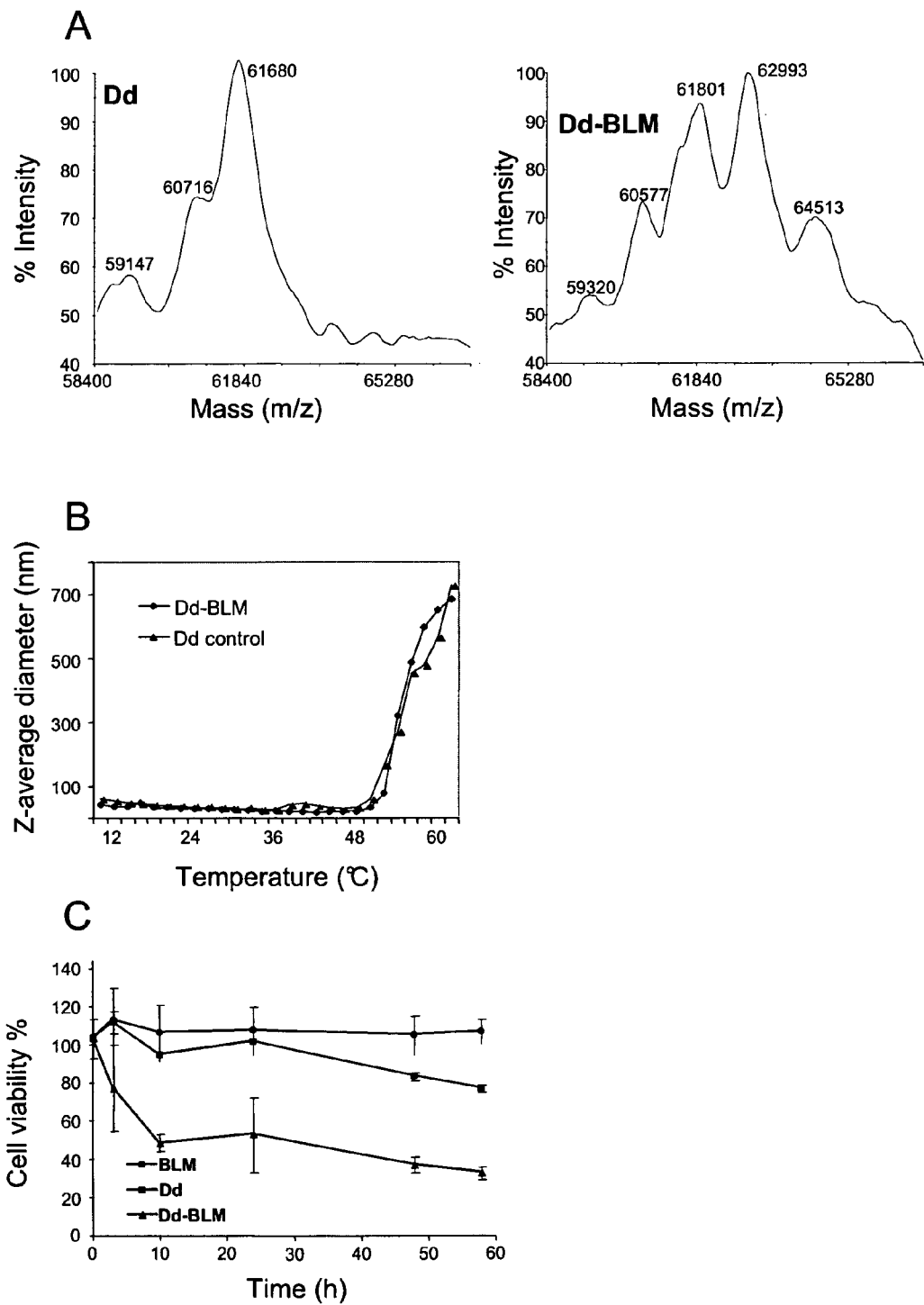
FIG. 4 shows the cytotoxicity of bleomycin delivered by the Dd. Bleomycin has been chemically attached to the Dd (as discussed in Example IV). (A) Analysis of the Dd-BLM conjugate using mass spectrometry. (B) Analysis of the Dd-BLM conjugate using dynamic light scattering. (C) MTT cytotoxicity test. HeLa cells were treated with: free BLM (0.13 µM), Dd (1 µg) and Dd-BLM (1 µg, which delivers 0.08 µM BLM), according to Example IV.

More than 60% of human cells in in vitro cultures are destroyed after Dd-BLM treatment. The cytotoxic effect was not observed when free bleomycin was applied in doses equivalent to the antibiotic quantity contained in the preparation used. The Dd-BLM preparations containing about 0.08 μM BLM were proved to be highly cytotoxic, whereas free BLM added in the same quantity had no cytotoxic effect (FIG. 4). Similar cell mortality was observed only when 8 μM of free BLM solution (results not shown) was added, that is, 100 times more than in the case of bleomycin delivered by Dds.

The subsequent stage included microscopic examination of human cancer cells subjected to Dd-BLM treatment. In order to prepare preparations for the confocal microscope, HeLa cells ($5 \times 10^4$) were plated onto special coverslips. On the next day, various amounts of pure Dd, Dd-BLM conjugate or free bleomycin were applied onto the cells; all samples were suspended in the serum-free EMEM medium. After 3-hour incubation, foetal bovine serum was added to a final concentration of 10%. After the end of incubation, the cells were washed with cold PBS and subsequently fixed and permeabilised for 10 min in 100% cold methyl alcohol. Preparations obtained in this way were incubated for 1 hour with antibodies (Ab): polyclonal Dd-recognising Ab, monoclonal tubulin-recognising Ab (Sigma, St Louis Mo., USA) and polyclonal anti-γ-H2AX Ab (Calbiochem, Darmstadt, Germany). After washing the cells using PBS, secondary antibodies were applied, conjugated with dyes: Texas Red (Jackson, ImmunoResearch Laboratories, West Grove Pa., USA) or green, FITC (Santa Cruz Biotechnology, Santa Cruz Calif., USA). DAPI solution was used for the labelling of cell nuclei (Applichem).

Figure 5A:
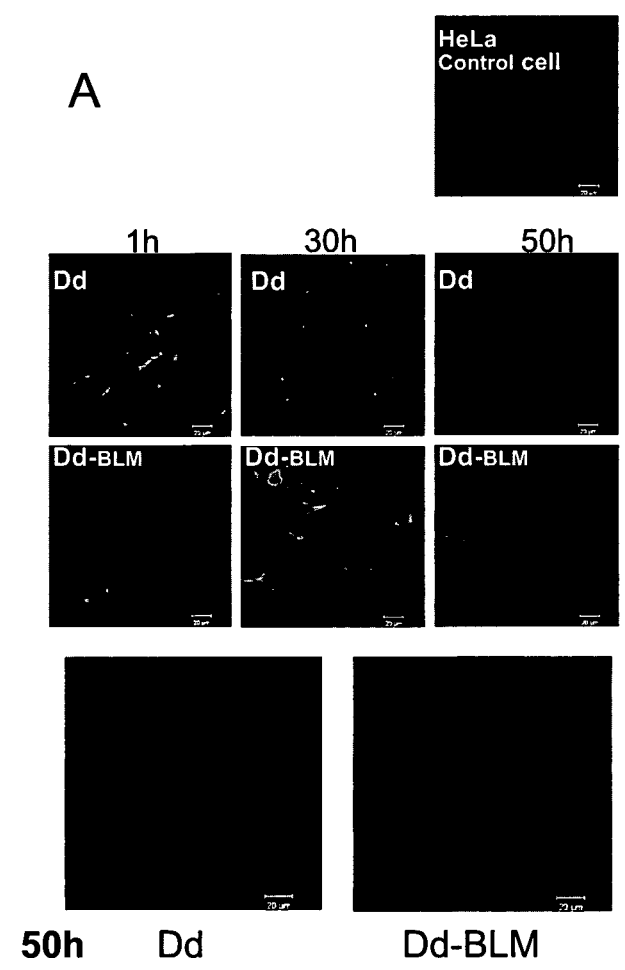
FIG. 5 shows the effect of Dd-BLM activity on HeLa cells. (A) Cells treated with Dd or Dd-BLM (1 µg sample) were analysed under a confocal microscope using a Dd-recognising antibody (red signal, white/grey on black and white photographs). Cell nuclei were stained with DAPI solution. The lowermost row shows cells after 50-hour treatment, without nuclear staining. The scale bar corresponds to 20 µm. (B). Cells treated with Dd, free bleomycin or Dd-BLM were analysed after a specified time under a confocal microscope using antibodies: anti-γ-H2AX (red signal in cell nuclei, grey on black and white photographs) and anti-tubulin (green signal in the cytoplasm, white/grey on black and white photographs). The scale bar corresponds to 10 µm.

Because no bleomycin-recognising antibody is available, which could be used in confocal microscopy, anti-Dd Abs were used for the detection of the Dd-BLM conjugate. The Dd and also Dd preparation with covalently bound BLM were found to penetrate into 100% cells in in vitro cultures, which is proved by the red signal from the anti-Dd antibody in the cytoplasm of cells observed 1 hour after the application of the preparations (FIG. 5A, 1 hour, Dd and Dd-BLM). Fifty hours after the application of the free Dd, the vector quantity (visible in the cytoplasm only) decreased significantly in comparison with shorter incubation times (red signal, FIG. 5A), which indicates proteolysis and elimination of the vector from cells. The Dd-BLM conjugate induces the occurrence of enlarged cells, which is visible 30 hours after conjugate application, being even more pronounced at a later time. Fifty hours after Dd-BLM application, the Dd signal is present throughout the cell, which indicates that nuclear membrane integrity has been destroyed (one of cell death symptoms).

Figure 5B:
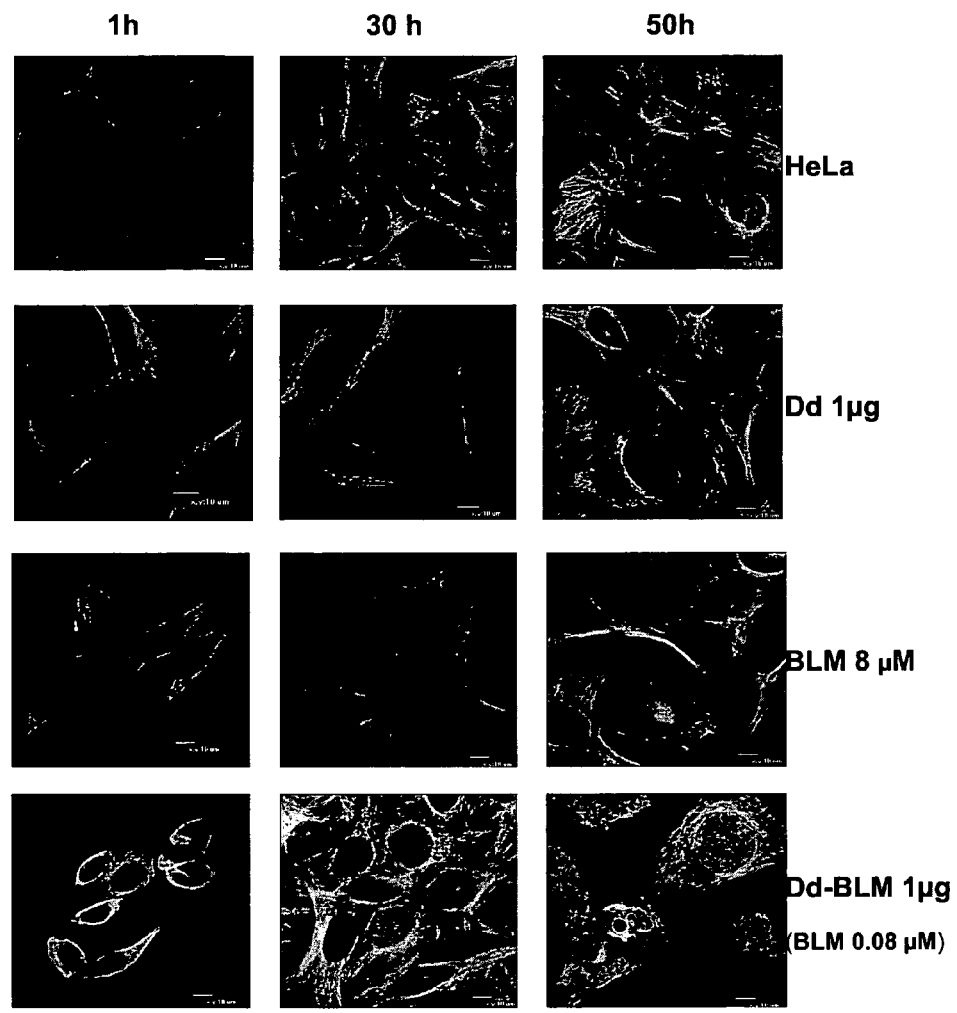
Figure 6:
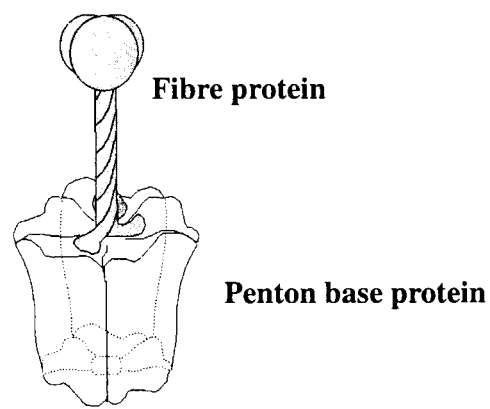

The cytotoxic, BLM activity is known to result from DNA damage (Mir et al., 1996). Phosphorylation of the C-terminal region of the H2AX histone in higher eukaryotic cells is one of chromatin modifications in response to double-strand DNA breaks (Kinner et al., 2008). A specific antibody, which recognises the phosphorylated histone form (anti-γ-H2AX; Calbiochem, Darmstadt, Germany) was used as the probe for detecting DNA damage. In control HeLa cells and in cells treated with a pure dodecahedron, no DNA damage was found, indicated by the lack of the red signal from the anti-γ-H2AX antibody (FIG. 5B, rows HeLa and Dd). Conversely, the Dd-BLM conjugate, when penetrating into cells, degrades nuclear DNA, which is indicated by the presence of the signal from the specific antibody. Application of free bleomycin has a similar effect (FIG. 5B, row: BLM). The effect of the action of 0.08 μM BLM-containing conjugate is stronger than damage induced by free BLM at a concentration of 8 μM and, therefore 100 times as high (FIG. 5B, rows: Dd-BLM and BLM).

REFERENCES

Carter B. J., de Vroom E., Long E. C., van der Marel G. A., van Boom J. H., Hecht S. M. (1990) Site-specific cleavage of RNA by Fe(II) bleomycin. Proc Natl Acad Sci USA. 87:9373-7.

Chen X. Multimodality imaging of tumor integrin alphav-beta3 expression. Mini Rev Med Chem. 2006 February; 6 (2):227-34.

Fender P., Ruigrok R. W., Gout E., Buffet S., Chroboczek J. (1997) Adenovirus dodecahedron, a new vector for human gene transfer. Nat. 15 (1), 52-56.

Fender P., Schoehn G., Foucaud-Gamen J., Gout E., Garcel A., Drouet E., ChroboczeK J. (2003) Adenovirus dodecahedron allows large multimeric protein transduction in human cells. J. Virol. 77 (8): 4960-4964.

Gehl J., Sorensen T. H., Nielsen K. (1999) In vivo electroporation of skeletal muscle: threshold, efficacy and relation to electric field distribution. Biochim. Biophys Acta 1428: 233-240.

Gothelf A., Mir M. and Gehl J. (2003) Electrochemotherapy: results of cancer treatment using enhanced delivery of bleomycin by electroporation. Canser Treatment Reviews 29:371-387.

Kinner A, Wu W, Staudt C, Iliakis G (2008) Gamma-H2AX in recognition and signaling of DNA double-strand breaks in the context of chromatin. Nucleic Acids Res 36: 5678-5694.

Lazo J. S. (1996) Bleomycin. In Chabner B. A. (ed.), Cancer Chemotherapy and Biotherapy. Lippincott-Raven Publishers. p379-393.

Lazo J. S., Sebti S. M. (1997) Bleomycin. Cancer Chemother Biol Response Modif. 17:40-5. Mir L. M., Tounekti O., Orlowski S. (1996) Bleomycin: revival of an old drug. Gen. Pharmacol. 27: 745-748.

Mosmann T (1983) Rapid colorimetric assay for cellular growth and survival: application to proliferation and cytotoxicity assays. J Immunol Methods 65: 55-63.

Orlowski S., Belehradek Jr J., Paoletti C. (1988) Transient electropermabilisation of cells in culture. Increase of the cytotoxicity of anticancer drugs. BiochemPphannacol. 37: 4727-4733.

Poddevin B., Orlowski S., Belehradek Jr J. (1991) Very high cytotoxicity of bleomycin introduced into the cytosol of cells in culture. Biochem. Pharmacol. 42 (suppl):67-75.

Vives R. R., Lortat-Jacob H., Chroboczek J., Fender P. (2004) Heparan sulfate proteoglycan mediates the selective attachment and internalization of serotype 3 human adenovirus dodecahedron. Virology 321:332-40.

Sausville E. A., Stein R. W., Peisach J., Horwitz S. B. (1978) Properties and products of the degradation of DNA by bleomycin and iron(II). Biochemistry 17:2746-54.

Song L, Nakaar V, Kavita U, Price A, Huleatt J, et al. (2008) Efficacious recombinant influenza vaccines produced by high yield bacterial expression: a solution to global pandemic and seasonal needs. PLoS ONE 3: e2257.

Tounekti O., Pron G., Belehradek Jr. J. (1993) Bleomycin, an apoptosis-mimetic drug that induces two types of cell death depending on the number of molecules internalized. Cancer Res. 53: 5462-5469.

The invention claimed is:

1. An adenoviral dodecahedron particle comprised of pentons or penton base proteins originating from a mammalian adenovirus, with at least two copies of a bleomycin glycopeptide covalently linked to the particle.

2. The particle of claim 1, wherein the bleomycin glycopeptide is bleomycin A5.

3. The particle of claim 1, wherein the bleomycin is cross-linked to the particle with carbodiimide.

4. The particle of claim 3, wherein the bleomycin is cross-linked to amine groups or cysteine residues of the dodecahedron, or to the N-terminus or C-terminus of a penton base protein, or a combination thereof.

5. The particle of claim 4, wherein at least 30 bleomycin residues are conjugated to one dodecahedron particle containing 60 base protein monomers.

6. A process for the manufacture of the particle of claim 1, comprising:
   producing dodecahedron particles in insect cells,
   purifying the particles using ultracentrifugation in a sucrose gradient and an ion-exchange column, and
   covalently linking at least two copies of a bleomycin glycopeptide to the purified dodecahedron particles.

7. The process of claim 6, wherein the bleomycin glycopeptide is bleomycin A5.

8. The process of claim 6, wherein the bleomycin is cross-linked to the particle with carbodiimide.

9. The process of claim 8, wherein the bleomycin is cross-linked to amine groups or cysteine residues of the dodecahedron, or to the N-terminus or C-terminus of a penton base protein, or a combination thereof.

10. The process of claim 9, wherein at least 30 bleomycin residues are conjugated to one dodecahedron particle containing 60 base protein monomers.

11. A pharmaceutical composition comprising the particle of any of claims 1-5.

12. A method of delivering bleomycin to a cell or tissue, comprising administering the particle of any of claims 1-5 to the cell or tissue.

13. The method of claim 12, wherein a cytotoxically effective dose of the dodecahedron-bleomycin particle is at least 50 times as low as free bleomycin.

14. A method of delivering bleomycin to a cell or tissue, comprising administering the pharmaceutical composition of claim 11 to the cell or tissue.

15. The method of claim 14, wherein a cytotoxically effective dose of the dodecahedron-bleomycin particle is at least 50 times as low as free bleomycin.

16. A method of inhibiting the proliferation of cancer cells, comprising delivering bleomycin to the cells by the method of claim 12.

17. A method of inhibiting the proliferation of cancer cells, comprising delivering bleomycin to the cells by the method of claim 14.

* * * * *